US00PP13275P2

(12) United States Plant Patent
Olesen et al.

(10) Patent No.: US PP13,275 P2
(45) Date of Patent: Nov. 26, 2002

(54) MINIATURE ROSE VARIETY 'POULRA002'

(76) Inventors: L. Pernille Olesen, Hillerødvejen 49, DK-3480 Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/780,095

(22) Filed: Feb. 8, 2001

(51) Int. Cl.[7] ..... A01H 5/00

(52) U.S. Cl. ..... Plt./121

(58) Field of Search ..... Plt./121, 116, 120

*Primary Examiner*—Bruce R. Campell
*Assistant Examiner*—June Hwu

(57) ABSTRACT

A new miniature rose plant which has abundant, salmon flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

BOTANICAL CLASSIFICATION

*Rosa hybrida* 'POULra002'.

SUMMARY OF THE INVENTION

The present invention constitutes a new and distinct variety of miniature rose plant which originated from a controlled crossing between 'POULhappy' (U.S. Plant Pat. No. 9,483 dated Mar. 26, 1996) and 'KORkleiva' (U.S. Plant Pat. No. 11,232 dated Feb. 22, 2000). The two parents were crossed and the resulting seeds were planted in a controlled environment. The new variety is named 'POULra002'.

The new rose may be distinguished from its seed parent, 'POULhappy', by the following combination of characteristics:

1. The flower color of 'POULhappy' is red, whereas 'POULra002' is salmon orange.
2. The petalage of 'POULhappy' is semi-double whereas the petalage of 'POULra002' is double.
3. The size of the blooms of 'POULhappy' is smaller than 'POULra002'.

The new variety may be distinguished from its pollen parent, 'KORkleiva' by the following combination of characteristics:

1. The color of 'KORkleiva's' blooms is creamy white, while the flower color of 'POULra002' is salmon.
2. The pollen parent has 1–3 blooms per flowering stem, whereas 'POULra002' has 3–5 blooms per flowering stem.

The objective of the hybridization of this rose variety for commercial culture was to create a new and distinct variety with unique qualities, such as:

1. Uniform and abundant salmon flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra002' from all other varieties of which we are aware.

As part of their rose development program, L. Pernille Olesen and Mogens N. Olesen germinated the seeds from the aforementioned hybridization in winter 1997 and conducted evaluations on the resulting seedlings in a controlled environment in Fredensborg, Denmark.

'POULra002' was selected by the inventors as a single plant from the progeny of the bybridization in spring 1998.

Asexual reproduction of 'POULra002' by cuttings and traditional budding was first done by L. Pernille and Mogens N. Olesen in their nursery in Fredensborg, Denmark in July, 1998. This initial and other subsequent propagations conducted in controlled environments have demonstrated that the characteristics of 'POULra002' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra002'. Specifically illustrated in SHEET 1:

FIG. 1. Stem with flower;

FIG. 2. Flower bud, partially opened bud, and open bloom;

FIG. 3. Flower petals, detached;

FIG. 4. Sepals, receptacle, and pedicel;

FIG. 5. Flowering stem as well as a bare stem exhibiting thorns;

FIG. 6. Leaves.

DETAILED DESCRIPTION OF THE VARIETY

The following is a description of 'POULra002', as observed in its growth in Burlington, Ontario, Canada, on plants aged 16 weeks. Color references are made using The Royal Horticultural Society (London, England) Colour Chart, 1995, except where common terms of color are used.

For a comparison, several physical sharacteristics of the rose variety 'POULoral', a rose variety from the same inventors described and illustrated in U.S. Plant Pat. No. 9,018 and issued on Dec. 20, 1994 are compared to 'POULra002' in Chart 1.

CHART 1

| | 'POULra002' | 'POULoral' |
|---|---|---|
| Length of bud upon opening | 18–20 mm | 13 mm |
| Size of open bloom | 45 mm | 40 mm |
| Blooms borne | Typically 3–5 per stem, rarely 1 flower per stem. | Singly and several together 3–5 flowers. |

Classification:

*Commercial*.—Miniature.

Parents: 'POULhappy'×'KORkleiva'.

FLOWER AND FLOWER BUD

Blooming habit: Continuous.

Flower bud:

*Size*.—Upon opening, 18–20 mm in length from base of receptacle to end of bud.

*Bud form*.—Short and pointed ovoid.

*Bud color*.—As sepals unfold, Red Group 47B. Red Group 50A at ¼ opening.

*Sepals*.—Green Group 144B. Moderate foliaceous appendages on 3 of the 5 sepals. Upper and lower surfaces of sepals moderately pubescent. Stipitate glands are present along sepal margins. Sepals are 12 cm long and 10 cm wide. Anthocyanin: On foliaceous appendages of juvenile sepals. Color: Greyed-Purple Group 183D.

*Receptacle*.—Surface: Smooth. Shape: Pear-shaped. Size: Small. 8 mm(h)×5–8 mm (w). Color: Green Group 144B.

*Peduncle*.—Surface: Stipitate glands present. Length: Variable. 5–20 mm. Color: Yellow-Green Group 144A. Strength: Erect. Anthocyanin: On bud; slight intonations of Greyed purple Group 183D.

*Borne*.—Multiple buds per stem, rarely a single bud per stem.

Flower bloom:

*Fragrance*.—Very light.

*Duration*.—As a pot plant, flowers last from 17 to 22 days. As a cut flower 8 to 10 days. The blooms have a duration on the plant of approximately 12 to 14 days.

*Size*.—Large for an 8–11 cm pot rose. Average flower diameter is 35–45 mm when open.

*Form*.—Shape of flower when viewed from the side: Upon opening, upper part: Flat. Upon opening, lower part: Flat. Open flower, upper part: Flat. Open flower, lower part: Flattened convex.

*Petalage*.—Very double. Average range: 35–45 petals under normal conditions with 0–4 petaloids.

Color:

*Upon opening, petals*.—Outermost petals: Outer Side: Red Group 47B. Inner Side: Red Group 43C. Innermost petals: Outer Side: Red Group 52A. Inner Side: Red Group 43C.

*Upon opening, basal petal spots*.—Outermost petals: Outer Side: Green-Yellow Group 1C. Inner Side: Yellow Group 2B with outer edge of petal spot White Group 155A. Innermost petals: Outer Side: Yellow-Green Group 154D. Inner Side: Yellow-Green Group 154D with outer edge of petal spot White Group 155A.

*After opening, petals*.—Outermost petals: Outer Side: Red Group 52B. Inner Side: Red Group 52C to 50B. Innermost petals: Outer Side: Red Group 52B. Inner Side: Red Group 48C.

*After opening, basal petal spots*.—Outermost petals: Outer Side: Yellow Group 1B with outer edge of petal spot Red Group 56D. Inner Side: Yellow Group 1B with outer edge of petal spot Yellow Group 4D. Innermost petals: Outer Side: Yellow Group 3C. Inner Side: Yellow Group 4A.

General tonality: On open flower, Red Group 43C. No change in the general tonality at the end of the $8^{th}$ day. Afterwards, general tonality is Red Group 43D.

Petals:

*Petal reflex*.—Reflexed downward.

*Petal edge*.—Uniform.

*Shape*.—Deltoid. Apex is rounded. Base is flat at union with peduncle.

*Size*.—10 mm long and 8 to 10 mm wide.

*Texture*.—Smooth.

*Petaloids*.—Present. Quantity: 0–4. Size: 5 mm wide and 5 mm long. Shape: Rounded, occasionally irregular. Color: Upper surface is Red Group 43C; lower surface is Red Group 43C. Texture: Smooth.

*Thickness*.—Thick.

*Arrangement*.—Imbricated.

Reproductive organs:

*Pollen*.—Color: Greyed-Orange Group 167A–B. Quantity: Limited.

*Anthers*.—Size: 1 to 2 mm long. Color: Greyed-Yellow Group 160B with intonations of Greyed-Red Group 181B. Quantity: 25 to 30.

*Filaments*.—Color: Yellow-Orange Group 17B–C. Length: 5 to 7 mm.

*Stigmas*.—Location inferior to the anthers. Color: Yellow-Green Group 145C. Quantity: 15 to 20. Size: 1 mm long.

*Styles*.—Color: Yellow-Green Group 145B. Length: 3 to 4 mm.

*Hip formation*.—Not observed.

PLANT

Plant growth: Vigorous, and compact. When grown as an 8–11 cm pot plant, the average height of the plant is 15–20 cm and the average width is 18–20 cm.

Stem:

*Color*.—Young wood: Yellow-Green Group 146A. Older wood: Yellow-Green Group 146B.

*Prickles*.—Incidence: Very few. Size: Average length: 2–3 mm. Color: Greyed-Red Group 180D. Shape: Concave.

*Surface*.—Young wood: Smooth. Older wood: Smooth.

Plant foliage: Typical number of leaflets on normal leaves in middle of the stem: 5 leaflets with 7 leaflets per leaf also observed.

Typical leaf size: Small. 75–100 mm (l)×45–50 mm (w).

*Quantity*.—Very abundant.

*Color*.—Mature Foliage: Upper Leaf Surface: Yellow-Green Group 147A. Lower Leaf Surface: Yellow-Green Group 147B. Juvenile foliage: Upper Leaf Surface: Yellow-Green Group 147A. Lower Leaf Surface: Yellow-Green 147C.

*Anthocyanin intonation*.—Location: Along the margins of juvenile leaflets and on the reverse side of mature foliage. Color: Greyed-Red Group 180C.

Plant leaves and leaflets:

*Stipules*.—Size: 9 mm (l)×3–4 mm (w). Color: Green Group 143C. Presence of stipitate glands: Very few located along margins of stipules.

*Anthocyanin*.—Mature foliage: Very slight intonation of Greyed-Red Group 180D at base and along margins of stipules. Juvenile foliage: Intonations of Greyed-Red Group 181C along margins of stipules.

*Petiole*.—Length: 18–25 mm. Color: Yellow-Green Group 144A. Underneath: Smooth. Margins: Stipitate glands present. Anthocyanin: Intonations of Greyed-Purple Group 183B on upper surface of juvenile foliage.

*Rachis*.—Color: Yellow-Green Group 144B. Underneath: Few small prickles present. Margins: Limited number of stipitate glands present. Anthocyanin: Very light intonations of Greyed-Purple Group 183D on mature foliage at leaflet attachments. Juvenile foliage has stronger intonations of Greyed-Purple Group 183D on upper surface.

*Leaflet*.—Edge: Serrated. Shape: Ovate. Apex: Acute. Base: Rounded. Other: Moderately glossy and thin.

Disease resistance: Above average resistance to mildew, black spot, and Botrytis under normal growing conditions in Burlington, Canada.

We claim:

1. A new and distinct variety of rose plant of the miniature class, substantially as herein illustrated and described as a distinct and novel rose variety due to its abundant, salmon-colored flowers, vigorous growth, compact habit, suitability for production from softwood cuttings in pots, and durable flowers and foliage which make the variety suitable for distribution in the floral industry.

* * * * *

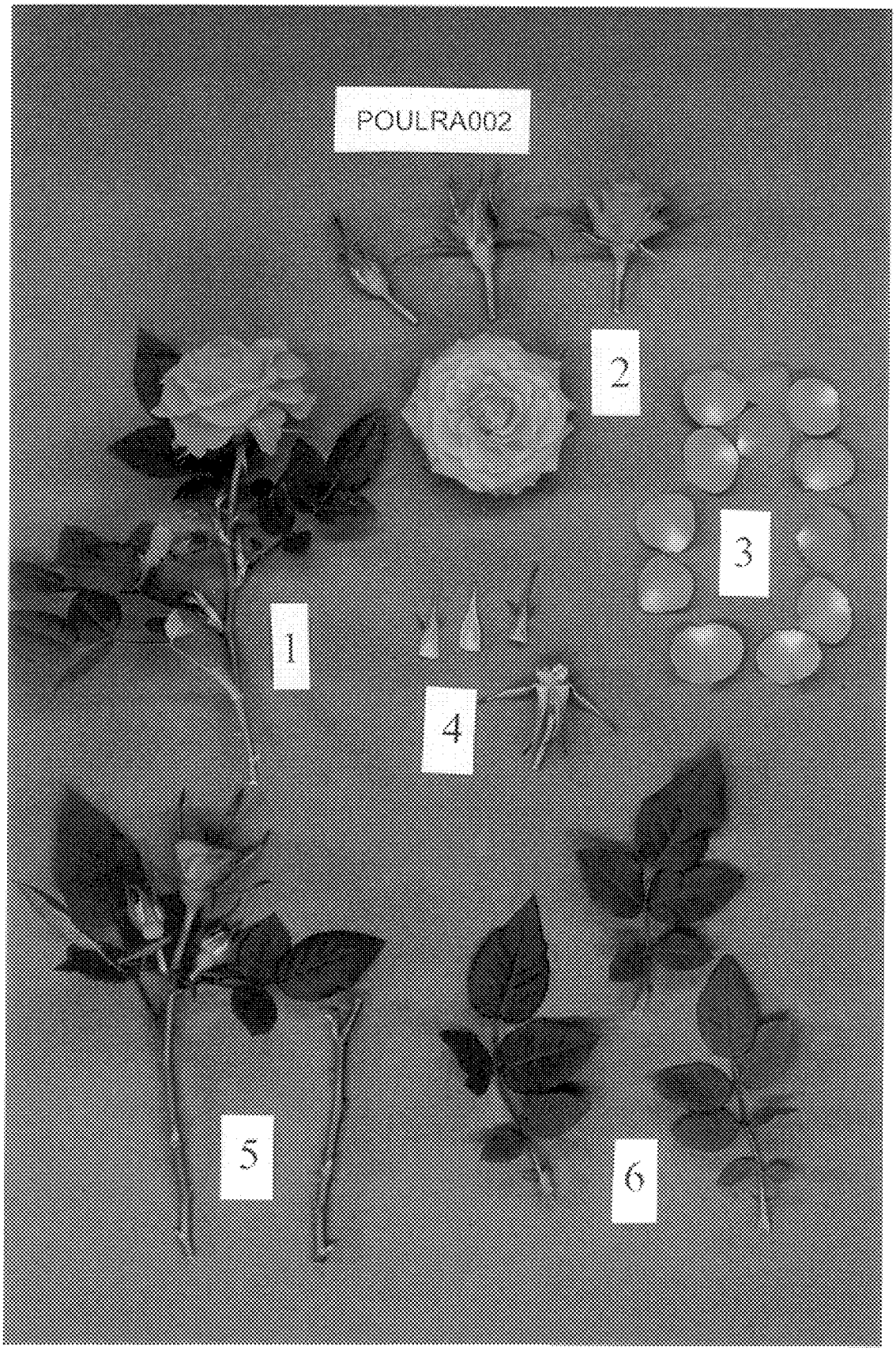
POULRA002
2
3
1
4
5
6